United States Patent
Murahashi et al.

(10) Patent No.: US 6,486,340 B2
(45) Date of Patent: Nov. 26, 2002

(54) METHOD FOR PRODUCING AN α-AMINONITRILE FROM A TERTIARY ANIME AND A CYANIDE THROUGH OXIDATION WITH OXYGEN BY USING A TRANSITION METAL CATALYST

(75) Inventors: Shun-ichi Murahashi, Ikeda (JP); Naruyoshi Komiya, Ashiya (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 09/906,733

(22) Filed: Jul. 18, 2001

(65) Prior Publication Data

US 2002/0042534 A1 Apr. 11, 2002

(30) Foreign Application Priority Data

Jul. 19, 2000 (JP) ........................... 2000-218544

(51) Int. Cl.[7] ............................................. C07C 255/00
(52) U.S. Cl. ........................................................ 558/348
(58) Field of Search ........................................... 558/348

(56) References Cited

FOREIGN PATENT DOCUMENTS

JP 11255729 9/1999

OTHER PUBLICATIONS

Murata, S., et al., *Iron–Catalyzed Oxidation of 4–Substituted N,N–Dimethylanilines with Molecular Oxygen in the Presence of Benzoyl Cyanide*, Bull. Chem. Soc. Jpn., 66, 1297–1298 (1993), Japan.

*Primary Examiner*—T. A. Solola
*Assistant Examiner*—Joseph Murray
(74) *Attorney, Agent, or Firm*—Burns, Doane, Swecker & Mathis LLP

(57) ABSTRACT

A method for producing an α-aminonitrile, is disclosed, which method includes the step of oxidizing a tertiary amine with oxygen by using a transition metal catalyst in the presence of a cyanide. The α-aminonitrile thus obtained can be easily converted to amino acids as well as various nitrogen-containing physiologically active materials.

16 Claims, No Drawings

METHOD FOR PRODUCING AN α-AMINONITRILE FROM A TERTIARY ANIME AND A CYANIDE THROUGH OXIDATION WITH OXYGEN BY USING A TRANSITION METAL CATALYST

BACKGROUND OF THE INVENTION

1. Field of the Invention

The present invention relates to a method for producing an α-aminonitrile by aerobic oxidation of a tertiary amine with a cyanide by using a transition metal catalyst.

2. Related Art Statement

In the fields of medicinal and material sciences, the necessity for the nitrogen-containing organic compounds has been increasing in recent years, and development of efficient and selective methods for constructing carbon skeletons of nitrogen-containing organic compounds has been urgently required. An α-aminonitrile is obtained by cyanating carbon at a position adjacent to a nitrogen atom of a tertiary amine through catalytic oxidation with oxygen. Since this α-aminonitrile is easily converted to an amino acid as well as various nitrogen-containing biologically active materials, the utility of the reaction is high.

It is known that such α-aminonitriles are obtained by employing anode oxidation (J. Am. Chem. Soc. 91, 4181 (1969), a photo reaction (Tetrahedron Lett. 31, 4735 (1990), chlorine dioxide (J. Am. Chem. Soc. 110, 4829 (1988), a benzoiodine xole (Tetrahedron Lett. 36, 7975 (1995)), or cyano iodine or the like. However, the above reactions are not industrially proper methods, since these should employ special reaction apparatuses, special reaction reagents that are difficult to obtain a large amount.

The present inventors discovered a method for producing α-aminonitriles by the reaction of tertiary amines with trimethylsilyl cyanide in the presence of ruthenium chloride and peracetic acid (Japanese Chemical Society No. 70 Spring Season Annual Report 3J247). However, this method since it uses relatively expensive trimethylsilyl and peracetic acid and gives many byproducts needed further improvement for an industrial process. After further investigation in view of this, the present inventors discovered a method for producing α-aminonitriles from tertiary amines by using metal cyanides and hydrogen peroxide both of which are inexpensive and easily available (JP-A 11-255,729). Although this method can produce the α-aminonitriles relatively inexpensively, the efficient method using molecular oxygen, a method using a safer and cheaper oxidant, has been demanded to be developed.

SUMMARY OF THE INVENTION

Having examined oxidizing agents that satisfies sufficient safety and economy for industry process, the present inventors discovered that α-aminonitriles are obtained by oxidizing tertiary amines with molecular oxygen, and reached the invention based on this discovery. That is, the present invention is to provide a method for producing an α-aminonitrile, comprising the step of oxidizing a tertiary amine with oxygen by using a transition metal catalyst in the presence of a cyanide.

DETAILED DESCRIPTION OF THE INVENTION

(1) Tertiary Amines

As the tertiary amine for a starting material is preferable a tertiary amine that is represented by a general formula $R^1R^2NCH_2R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

(1-1) Substituting Group $R^1$

As the phenyl group, which may be substituted, in the substituting group $R^1$ of the compound represented by the general formula $R^1R^2NCH_2R^3$, mention may be made of, for example, phenyl group, lower alkyl-substituted phenyl groups such as 2-methylphenyl group, 3-methylphenyl group and 4-methylphenyl group, halogen-substituted phenyl groups such as 2-chlorophenyl group, 3-chlorophenyl group, 4-chlorophenyl group, 2-bromophenyl group, 3-bromophenyl group and 4-bromophenyl group, lower alkoxyphenyl groups such as 2-methoxyphenyl group, 3-methoxyphenyl group and 4-methoxyphenyl group, etc.

(1-2) $R^2$, $R^3$, etc.

As the alkyl groups for $R^2$ and $R^3$, mention may be made of, for example, methyl group, ethyl group, n-propyl group, i-propyl group, n-butyl group, s-butyl group, t-butyl group, pentyl group, hexyl group and cyclohexyl group. As the phenyl group which may be substituted, mention may be made of, for example, phenyl group, lower alkyl-substituted phenyl groups such as 2-methylphenyl group, 3-methylphenyl group and 4-methylphenyl group, halogen-substituted phenyl groups such as 2-chlorophenyl group, 3-chlorophenyl group, 4-chlorophenyl group, 2-bromophenyl group, 3-bromophenyl group and 4-bromophenyl group, lower alkoxyphenyl groups such as 2-methoxyphenyl group, 3-methoxyphenyl group and 4-methoxyphenyl group, etc.

As the nitrogen-containing ring which is formed when $R^2$ and $R^3$ are bonded to each other, mention may be made of piperidine, pyrrolidine, N-phenyl-1,2,3,4-tetrahydroisoquinoline, etc. As the nitrogen-containing ring which is formed when $R^1$ and $R^3$ are bonded to each other, mention may be made of 1, 2, 3, 4-tetrahydroisoquinoline, etc.

As specific examples for the tertiary amines, mention may be made of N,N-dimethylaniline, N-ethyl-N-methylaniline, N,N-diethylaniline, N-phenyl-N-methylaniline, N,N,4-trimethylaniline, N,N-dimethyl-4-bromoaniline, N,N-dimethyl-4-methoxyaniline, N-phenylpiperidine, N-(4-methoxyphenyl)piperidine, N-phenyl-1,2,3,4-tetrahydroisoquinoline, 6-benzyloxy-N-phenyl-7-methoxy-1, 2,3,4-tetrahydroxyisoquinoline, etc.

(2) Cyanide

As the cyanide for a starting material, alkali metal cyanides such as sodium cyanide and potassium cyanide, hydrogen cyanide or trimethylsilyl cyanide is preferred. From the reactivity and economical points of view, sodium cyanide and potassium cyanide are preferably used.

Although the use amount of the cyanide is not particularly limited, it is ordinarily 1 to 10 times in mole, preferably 1 to 3 times in mole as much as that of a substrate (tertiary amine). The cyanide may be used as it is, or in the form of a solution in which the cyanide is dissolved in a solvent mentioned later.

(3) α-Aminonitrile

The α-aminonitrile obtained in the present invention is preferably represented by a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring. Those recited in the above (1-1) and (1-2) are employed as specific examples for the $R^1$, $R^2$ and $R^3$.

As specific examples for the α-aminonitrile of the general formula $R^1R^2NCH(CN)R^3$ produced by the present invention, mention may be made of, for example, N-phenyl-N-methylaminoacetonitrile, N-phenyl-N-ethylamino-acetonitrile, 2-(N-ethyl-N-phenylamino)propionitrile, N,N-diphenylamino-acetonitrile, N-(4-methylphenyl)-N-methylaminoacetonitrile, N-(4-bromophenyl)-N-methylaminoacetonitrile, N-(4-methoxyphenyl)-N-methylaminoacetonitrile, 2-cyano-N-phenylpiperidine, 2-cyano-N-(4-methoxyphenyl)piperidine, 1-cyano-N-phenyl-1, 2,3,4-tetrahydroxyisoquinoline, 1-cyano-6-benzyloxy-N-phenyl-7-methoxy-1, 2,3,4-tetrahydroisoquinoline, etc.

(4) Transition Metal Catalysts

As the transition metal catalyst used in the present invention, one or more transition metal catalysts selected from the group consisting of a ruthenium-based catalyst, a chromium-based catalyst, a manganese-based catalyst, an iron-based catalyst, a cobalt-based catalyst, a nickel-based catalyst and a palladium-based catalyst are preferred. For example, use may be made of ruthenium catalysts such as $RuCl_3$-$nH_2O$, n-$Pr_4NRuO_4$, $Ru_2(\mu\text{-}OAc)_4Cl$, $Ru_3(\mu\text{-}O)(\mu\text{-}OAc)_6(H_2O)_3$, $RuO_2$, $KRuO_4$, $RuCl_2(PPh_3)_3$, $RuCl_2(bpy)_2$, $Ru(acac)_3$ and $K_4Ru(CN)_6$, chromium-based catalyst such as $CrCl_2$, manganese-based catalysts such as $MnCl_2$, iron-based catalysts such as $FeCl_3$, cobalt-based catalysts such as $CoCl_2$, nickel-based catalysts such as $NiCl_2$ and palladium-based catalysts such as $PdCl_2$. Among them, $RuCl_3$-$nH_2O$ is preferably used. Either anhydrides or hydrates of them may be employed. The use amount of the transition metal catalyst is ordinarily not less than 0.01 mol % relative to a substrate (tertiary amine), and no value is posed upon its upper limit. However, the use amount is preferably in a range of 1 to 5 mol %.

(5) Oxygen

Oxygen to be used in the present reaction may be supplied in the form of oxygen gas, a mixture of oxygen and an inert gas such as nitrogen or air, preferably at an oxygen pressure of 1 atm. Oxygen may be at a reduced or pressurized pressure.

(6) Others (6-1) Solvent

A solvent may be used in the present reaction. As the solvent, hydrocarbons (hexane, heptane, toluene, benzene, etc.), halogenated hydrocarbons (methylene chloride, chloroform, 1,2-dichloroethane, chlorobenzene, etc.), ketones (acetone, etc.), esters (ethyl acetate, etc.), alcohols (methanol, ethanol, n-propanol, i-propanol, n-butanol, s-butanol, t-butanol, n-pentanol, etc.), carboxylic acids (acetic acid, propionic acid, butanoic acid, pentanoic acid, etc.), etc. These compounds may be used singly or as a mixture of two or more of them. Preferably, a mixed solvent of an alcohol and a carboxylic acid may be recited, and its mixing ratio (alcohol/carboxylic acid) is ordinarily 0.01 to 100, preferably 0.1 to 10.

(6-2) Reacting Condition

The reaction temperature is ordinarily −50° C. to 100° C., preferably 20° C. to 100° C., more preferably 50° C. to 80° C. The reaction time is longer as the reaction temperature descends, whereas it is short as the reaction temperature rises. The reaction time is appropriately determined depending upon the reacting temperature.

EXAMPLES

In the following, the method for effecting the cyanation reaction will be first explained, which is however not intended to limit the present invention. In the following, all the reactions and extracting operations were performed inside a draft having good ventilation.

Example 1

Cyanation of N,N-Dimethyl-4-bromoaniline

N,N-dimethyl-4-bromoaniline (1 mmol), $RuCl_3$-$nH_2O$ (0.05 mmol) and sodium cyanide (1.2 mmol) were charged into a 25-ml side-arm flask, the interior of the reacting container was replaced by oxygen, and an oxygen balloon was attached to supply oxygen at 1 atm. Then, 1.7 ml of a mixed solvent of methanol-acetic acid (volume ratio 3/1) was added thereto at room temperature. Reaction was effected by stirring the mixed liquid at 60° C. for 2 hours. After the reaction mixture liquid was made alkaline with the addition of saturated sodium bicarbonate aqueous solution, the mixture was extracted with 10 ml ethyl acetate once and with 5 ml ethyl acetate twice. The extracted liquid thus obtained was washed with saturated saline solution, and dried over sodium sulfate, thereby obtaining an ethyl acetate solution of N-(4-bromophenyl)-N-methylaminoacetonitrile. This solution was analyzed by a gas chromatography internal standard method, which revealed the conversion rate of N,N-dimethyl-4-bromoaniline being 98% with a yield of N-(4-bromophenyl)-N-methylaminoacetonitrile being 82% (vs. N,N-dimethyl-4-bromoaniline). After this solution was concentrated under reduced pressure, the concentrated liquid was treated with a silica gel chromatography. Thereby, N-(4-bromophenyl)-N-methylaminoacetonitrile was isolated at a yield of 72%.

Example 2

Cyanation of N,N-Dimethylaniline

N,N-dimethylaniline (1 mmol), $RuCl_3$-$nH_2O$ (0.05 mmol) and sodium cyanide (1.2 mmol) were charged into a 25-ml side-arm flask, the interior of the reacting container was replaced by oxygen, and an oxygen balloon was attached to supply oxygen at 1 atm. Then, 1.7 ml of a mixed solvent of methanol-acetic acid (volume ratio 3/1) was added thereto at room temperature. Reaction was effected by stirring the mixed liquid at 60° C. for 2 hours. After the reaction mixture liquid was made alkaline with the addition of saturated sodium bicarbonate aqueous solution, the mixture was extracted with 10 ml ethyl acetate once and with 5 ml ethyl acetate twice. The extracted liquid thus obtained was washed with saturated saline solution, and dried over sodium sulfate, thereby obtaining an ethyl acetate solution of N-phenyl-N-methylaminoacetonitrile. This solution was analyzed by the gas chromatography internal standard method, which revealed a conversion rate of N,N-dimethylaniline being 99% with a yield of N-phenyl-N-methylaminoacetonitrile being 93% (vs. N,N-dimethylaniline).

Example 3

Cyanization of N,N,4-Trimethylaniline

N,N,4-trimethylaniline (1 mmol), $RuCl_3$-$nH_2O$ (0.05 mmol) and sodium cyanide (1.2 mmol) were charged into a 25-ml side-arm flask, the interior of the reacting container was replaced by oxygen, and an oxygen balloon was attached to supply oxygen at 1 atm. Then, 1.7 ml of a mixed solvent of methanol-acetic acid (volume ratio 3/1) was added thereto at room temperature. Reaction was effected by stirring the mixed liquid at 60° C. for 1 hour. After the reaction mixture liquid was made alkaline with the addition of saturated sodium bicarbonate aqueous solution, the mixture was extracted with 10 ml ethyl acetate once and with 5 ml ethyl acetate twice. The extracted liquid thus obtained was washed with saturated saline solution, and dried over sodium sulfate, thereby obtaining an ethyl acetate solution of N-(4-methoxyphenyl)-N-methylamino-acetonitrile. This solution was analyzed by the gas chromatography internal standard method, which revealed the conversion rate of N,N,4-trimethylaniline being 99% with a yield of N-(4-methylphenyl)-N-methylaminoacetonitrile being 97% (vs. N,N,4-trimethylaniline).

Example 4

Cyanation of N,N-Dimethyl-4-methoxyaniline

N,N-dimethyl-4-methoxyaniline (1 mmol), $RuCl_3$-$nH_2O$ (0.05 mmol) and sodium cyanide (1.2 mmol) were charged into a 25-ml side-arm flask, the interior of the reacting container was replaced by oxygen, and an oxygen balloon was attached to supply oxygen at 1 atm. Then, 1.7 ml of a mixed solvent of methanol-acetic acid (volume ratio 3/1) was added thereto at room temperature. Reaction was effected by stirring the mixed liquid at 60° C. for 4 hours. After the reaction liquid mixture was made alkaline with the addition of saturated sodium bicarbonate aqueous solution, the mixture was extracted with 10 ml ethyl acetate once and with 5 ml ethyl acetate twice. The extracted liquid thus obtained was washed with saturated saline solution, and dried over sodium sulfate, thereby obtaining an ethyl acetate solution of N-(4-methoxyphenyl)-N-methylaminoacetonitrile. This solution was analyzed by a gas chromatography internal standard method, which revealed the conversion rate of N,N-dimethyl-4-methoxyaniline being 80% with a yield of N-(4-methoxyphenyl)-N-methylaminoacetonitrile being 65% (vs. N,N-dimethyl-4-methoxyaniline).

Example 5

Cyanation of N-Ethyl-N-methylaniline

N-ethyl-N-methylaniline (1 mmol), $RuCl_3$-$nH_2O$ (0.05 mmol) and sodium cyanide (1.2 mmol) were charged into a 25-ml side-arm flask, the interior of the reacting container was replaced by oxygen, and an oxygen balloon was attached to supply oxygen at 1 atm. Then, 1.7 ml of a mixed solvent of methanol-acetic acid (volume ratio 3/1) was added thereto at room temperature. Reaction was effected by stirring the mixed liquid at 60° C. for 24 hours. After the reaction mixture liquid was made alkaline with the addition of saturated sodium bicarbonate aqueous solution, the mixture was extracted with 10 ml ethyl acetate once and with 5 ml ethyl acetate twice. The extracted liquid thus obtained was washed with saturated saline solution, and dried over sodium sulfate, thereby obtaining an ethyl acetate solution of N-phenyl-N-ethylaminoacetonitrile and 2-(N-methyl-N-phenylamino)propionitrile. This solution was analyzed by a gas chromatography internal standard method, which revealed the conversion rate of N-ethyl-N-methylaniline being 70% with a yield of N-phenyl-N-ethylaminoacetonitrile being 57% (vs. N-ethyl-N-methylaniline) and that of 2-(N-methyl-N-phenylamino)propionitrile being 7% (vs. N-ethyl-N-methylaniline).

Example 6

Cyanation of N-Phenyl-1,2,3,4-tetrahydroisoquinoline

N-phenyl-1,2,3,4-tetrahydroisoquinoline (1 mmol), $RuCl_3$-$nH_2O$ (0.05 mmol) and sodium cyanide (1.2 mmol) were charged into a 25-ml side-arm flask, the interior of the reacting container was replaced by oxygen, and an oxygen balloon was attached to supply oxygen at 1 atm. Then, 1.7 ml of a mixed solvent of methanol-acetic acid (volume ratio 3/1) was added thereto at room temperature. Reaction was effected by stirring the mixed liquid at 60° C. for 4 hours. After the reaction mixture liquid was made alkaline with the addition of saturated sodium bicarbonate aqueous solution, the mixture was extracted with 10 ml ethyl acetate once and with 5 ml ethyl acetate twice. The extracted liquid thus obtained was washed with saturated saline solution, and dried over sodium sulfate, thereby obtaining an ethyl acetate solution of 1-cyano-N-phenyl-1,2,3,4-tetrahydroisoquinoline. After this solution was concentrated under reduced pressure, the mixture was analyzed by a $^1H$ NMR internal standard method, which revealed the conversion rate of N-phenyl-1,2,3,4-tetrahydroisoquinoline being 91% with a yield of 1-cyano-N-phenyl-1,2,3,4-tetrahydroisoquinoline being 79% (vs. N-phenyl-1,2,3,4-tetrahydroisoquinoline). By using silica gel chromatography, 1-cyano-N-phenyl-1,2,3,4-tetrahydroisoquinoline was isolated at a yield of 76%.

According to the producing method of the present invention, the α-aminonitriles useful as intermediates in the medical and agricultural fields can be industrially advantageously produced. That is, they can be easily produced. According to this method, the α-aminonitriles can be effectively produced in a very clean manner from the tertiary amines by using easily available inexpensive sodium cyanide and molecular oxygen without producing byproducts. The α-aminonitriles each obtained by cyanating the carbon at a position adjacent to the nitrogen atom of the tertiary amine can be easily converted to amino acids as well as various nitrogen-containing physiologically active materials and have high utility.

What is claimed is:

1. A method for producing an α-aminonitrile, comprising the step of oxidizing a tertiary amine with oxygen by using a transition metal catalyst in the presence of a cyanide selected from the group consisting of an alkali metal cyanide, hydrogen cyanide and trimethylsilyl cyanide.

2. The α-aminonitrile producing method set forth in claim 1, wherein the tertiary amine is represented by a general formula $R^1R^2NCH_2R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

3. The α-aminonitrile producing method set forth in claim 1, wherein said cyanide is sodium cyanide or potassium cyanide.

4. The α-aminonitrile producing method set forth in claim 2, wherein said transition metal catalyst is one or more transition metal catalysts selected from the group consisting of a ruthenium-based catalyst, a chromium-based catalyst, a manganese-based catalyst, an iron-based catalyst, a cobalt-based catalyst, a nickel-based catalyst and a palladium-based catalyst.

5. The α-aminonitrile producing method set forth in claim 1, wherein said transition metal catalyst is one or more transition metal catalysts selected from the group consisting of a ruthenium-based catalyst, a chromium-based catalyst, a manganese-based catalyst, an iron-based catalyst, a cobalt-based catalyst, a nickel-based catalyst and a palladium-based catalyst.

6. The α-aminonitrile producing method set forth in claim 3, wherein said transition metal catalyst is one or more transition metal catalysts selected from the group consisting of a ruthenium-based catalyst, a chromium-based catalyst, a manganese-based catalyst, an iron-based catalyst, a cobalt-based catalyst, a nickel-based catalyst and a palladium-based catalyst.

7. The α-aminonitrile producing method set forth in claim 2, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

8. The α-aminonitrile producing method set forth in claim 1, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

9. The α-aminonitrile producing method set forth in claim 3, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

10. The α-aminonitrile producing method set forth in claim 4, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

11. The α-aminonitrile producing method set forth in claim 5, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

12. The α-aminonitrile producing method set forth in claim 6, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

13. The α-aminonitrile producing method set forth in claim 2, wherein said cyanide is sodium cyanide or potassium cyanide.

14. The α-aminonitrile producing method set forth in claim 13, wherein said transition metal catalyst is one or more transition metal catalysts selected from the group consisting of a ruthenium-based catalyst, a chromium-based catalyst, a manganese-based catalyst, an iron-based catalyst, a cobalt-based catalyst, a nickel-based catalyst and a palladium-based catalyst.

15. The α-aminonitrile producing method set forth in claim 14, wherein said α-aminonitrile has a general formula $R^1R^2NCH(CN)R^3$ in which $R^1$ is a phenyl group which may be substituted, $R^1$ is an alkyl group or a phenyl group which may be substituted, $R^1$ is a hydrogen atom, an alkyl group or a phenyl group which may be substituted, provided that $R^1$ and $R^3$ or $R^2$ and $R^3$ may be bonded to form a nitrogen-containing ring.

16. The α-aminonitrile producing method set forth in claim 13, wherein said α-aminonitrile has a general formula $R^1R^2NCH(CN)R^3$ in which $R^1$ is a phenyl group which may be substituted, $R^2$ is an alkyl group or a phenyl group which may be substituted, $R^3$ is a hydrogen atom, an alkyl group or a phenyl group which may be substituted, provided that $R^1$ and $R^3$ or $R^2$ and $R^3$ may be bonded to form a nitrogen-containing ring.

* * * * *

UNITED STATES PATENT AND TRADEMARK OFFICE
CERTIFICATE OF CORRECTION

PATENT NO.   : 6,486,340 B2
DATED        : November 26, 2002
INVENTOR(S)  : Shun-ichi Murahashi et al.

It is certified that error appears in the above-identified patent and that said Letters Patent is hereby corrected as shown below:

<u>Title page, Item [54], and Column 1, line 3,</u>
Please delete "ANIME", and insert therefor -- AMINE --.

<u>Column 5,</u>
Line 13, please delete "N-(4-methoxyphenyl)-N-methylamino-acetonitrile" and insert therefor -- N-(4-methylphenyl)-N-methylaminoacetonitrile --.

<u>Column 8,</u>
Line 31, please delete "$R^1$", and insert therefor -- $R^2$ --.
Line 32, please delete "$R^1$", and insert therefor -- $R^3$ --.

Signed and Sealed this

Ninth Day of September, 2003

JAMES E. ROGAN
*Director of the United States Patent and Trademark Office*